(12) United States Patent
Wang et al.

(10) Patent No.: US 9,255,176 B2
(45) Date of Patent: Feb. 9, 2016

(54) SURFACE MODIFICATION OF POLYMERS VIA SURFACE ACTIVE AND REACTIVE END GROUPS

(71) Applicant: DSM IP ASSETS B.V., Te Heerlen (NL)

(72) Inventors: Shanger Wang, Fairfield, CA (US); Robert S. Ward, Orinda, CA (US); Yuan Tian, Alameda, CA (US); Xuwei Jiang, El Sobrante, CA (US); Keith McCrea, Concord, CA (US); Scott Curtin, Berkeley, CA (US)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/455,423

(22) Filed: Aug. 8, 2014

(65) Prior Publication Data

US 2014/0350184 A1 Nov. 27, 2014

Related U.S. Application Data

(62) Division of application No. 13/129,438, filed as application No. PCT/US2009/064560 on Nov. 16, 2009, now abandoned.

(60) Provisional application No. 61/115,337, filed on Nov. 17, 2008.

(51) Int. Cl.
*A61K 9/14* (2006.01)
*C08G 18/83* (2006.01)
(Continued)

(52) U.S. Cl.
CPC .............. *C08G 18/837* (2013.01); *C08G 18/08* (2013.01); *C08J 7/12* (2013.01); *C08J 7/14* (2013.01); *A61K 2800/61* (2013.01)

(58) Field of Classification Search
CPC .................................................. A61K 2800/61
See application file for complete search history.

(56) References Cited

U.S. PATENT DOCUMENTS 7,217,769 B2 5/2007 Zamora et al.
2003/0204230 A1 10/2003 Yang et al.

FOREIGN PATENT DOCUMENTS

| JP | 53-113194 | 10/1978 |
| JP | 61-126143 A | 6/1986 |
| WO | WO 01/17575 A1 | 3/2001 |

(Continued)

OTHER PUBLICATIONS

Goddard et al, Polymer surface modification for the attachment of bioactive compounds, Prog. Polym. Sci. 32 (2007) 698-725.*

(Continued)

*Primary Examiner* — Paul Dickinson
(74) *Attorney, Agent, or Firm* — Birch, Stewart, Kolasch & Birch, LLP

(57) ABSTRACT

Polymer surface modification method comprising the steps of first forming a surface of primary reactive end groups tethered to the polymer chain ends during fabrication of an article, and then modifying the reactive surface with bio-active molecules, hydrophilic and hydrophobic monomers, oligomers, or polymers to attain specific surface properties. Alternatively, a multifunctional coupling agent can be used to couple the primary reactive group to a second reactive group capable of reacting with a functional group associated with bio-active molecules, hydrophilic and hydrophobic monomers, oligomers, and polymers to attain specific surface properties. The invention involves bringing reactive endgroups to the surface with surface active spacer attached to the polymer chain end. The surface active spacer allows the migration and enrichment of reactive end groups to the surface during fabrication. The invention provides medical devices having a bio-interface with anti-thrombogenic properties, lubricity, selective adsorption, and antimicrobial properties.

1 Claim, 8 Drawing Sheets

Surface with Enriched Reactive End Groups X techered to a surface active spacer ∿∿∿

Molecule Q with fucntional group K

Modified surface with properties of molecule Q

(51) Int. Cl.
*C08J 7/12* (2006.01)
*C08J 7/14* (2006.01)
*C08G 18/08* (2006.01)

(56) References Cited

FOREIGN PATENT DOCUMENTS

| | | |
|---|---|---|
| WO | WO 2004/044012 A1 | 5/2004 |
| WO | WO 2007/142683 A2 | 12/2007 |
| WO | WO 2008/000429 A2 | 1/2008 |
| WO | WO 2008/150788 A1 | 12/2008 |

OTHER PUBLICATIONS

Castilho et al., "Influence of matrix activation and polymer coating on the purification of human IgG with protein A affinity membranes", Journal of Membrane Science, 172, 2000, pp. 269-277.

International Search Report, dated Mar. 18, 2010 in PCT/US2009/064560.

Klein, "Affinity membranes: a 10-year review", Journal of Membrane Science, 179, 2000, pp. 1-27.

Prucker et al., "Photochemical Attachment of Polymer Films to Solid Surfaces via Monolayers of Benzophenone Derivatives", J. Am. Chem. Soc., 121, 1999, pp. 8766-8770.

Ulbricht et al., "Surface Modification of Ultrafiltration Membranes by Low Temperature Plasma. I. Treatment of Polyacrylonitrile", Journal of Applied Polymer Science, vol. 56, 1995, pp. 325-343.

Ulbricht, "Advanced functional polymer membranes", Elsevier, Polymer 47, 2006, pp. 2217-2262.

Written Opinion of the International Searching Authority, dated Mar. 18, 2010 in PCT/US2009/064560.

* cited by examiner

SURFACE MODIFICATION OF POLYMERS VIA SURFACE ACTIVE AND REACTIVE END GROUPS

CROSS-REFERENCE TO RELATED APPLICATIONS

This application is a divisional of U.S. patent application Ser. No. 13/129,438 (filing date Aug. 9, 2011), now abandoned. U.S. patent application Ser. No. 13/129,438 is the national phase under 35 U.S.C. §371 of international application PCT/US2009/064560, filed Nov. 16, 2009. Priority is claimed under 35 U.S.C. §119 to U.S. provisional application Ser. No. 61/115,337, filed Nov. 17, 2008. The contents of the foregoing applications are expressly incorporated by reference in this divisional application.

FIELD OF THE INVENTION

This invention provides methods for modifying the surface properties of polymeric articles, by first forming a surface of reactive end groups tethered to the polymer chain ends during fabrication of an article, and subsequently reacting the reactive end group surface with bio-active molecules, hydrophilic and hydrophobic monomers, oligomers or polymers to attain specific surface properties. In an embodiment of the invention, a multifunctional coupling agent can be used to couple the primary reactive group to a second reactive group capable of reacting with a functional group associated with bio-active molecules, hydrophilic and hydrophobic monomers, oligomers and polymers to attain specific surface properties. This method of the invention involves bringing reactive end groups to the surface of the polymeric article with surface active spacers attached to the reactive end groups. The surface active spacers promote the migration and enrichment of reactive end groups at the surface during fabrication of an article. External measures including annealing and melt processing may be used to further promote the migration and enrichment of reactive end groups at the surface.

BACKGROUND OF THE INVENTION

The surface modification of a substrate with a biologically active molecules and synthetic polymers can change the substrate surface properties such as tissue and blood compatibility, lubricity, wettability, permeability, antimicrobial properties that are important to the efficacy and safety of the medical product. Of these surface modification techniques, covalently bonding of molecules that are of specific characteristics is know to have the following advantages. i) This surface modification technique is advantageous in that a stable bond is formed between a surface and the modifier; and ii) Characteristic properties can be exhibited that are attributable to a large difference in affinity for material existing between a covalently bonded and topically coated. The process is often described as 'grafting' to differentiate from the surface alternation by ordinary spreading and solidifying.

Various grafting techniques have been proposed for the application of surface grafted polymers having aforementioned advantages by making use of their characteristic properties. Often, two alternative approaches are distinguished: "grafting-to"—attaching polymers to the solid surface, and "grafting-from"—monomers being polymerized from solid surface using an initiation at the surface. See Prucker et al., *J. Am. Chem. Soc.*, 1999: 121: 8766-70. Regardless of which technique is used, the solid surface must have reactive sites in an area accessible to the grafting monomers and polymers. This often requires additional steps of surface preparation prior to the grafting to provide the initiation sites for "grafting-from" reaction or have function groups available for "grafting-to" attachment.

Physical activation of chemical reactions, especially via controlled degradation of polymer on the substrate surface has been attempted in many different ways by using high energy radiation, e.g. β- or electron, plasma, UV irradiation. For example, U.S. Pat. No. 5,094,876 describes the method of modifying the plastic surfaces using gamma or electron beam irradiation induced chemical grafting. The method comprises the steps of pre-soaking the substrate in a monomer or a monomer solution to facilitate diffusion of said monomer or monomers into said plastic surface. The method lacks the chemical interaction of pre-formed substrate with the formed polymer and requires the use of organic solvent to facilitate diffusion of the monomers to the substrate and therefore poses the difficulty of removing the organic solvent afterwards.

WO 01/17575 A1 describes the radiation method of grafting hydrogel onto organic substrates. It involves steps of exposing a substrate to an initiator to generate reactive radical sites on the surface for graft polymerization of monomers immersed in thereby forming covalent bonds between monomer molecules and the substrate at reactive radical sites on the substrate surface. This "grafting-from" method calls for a separate step of surface preparation and may not applicable to many radical inert polymer substrates.

Plasma initiated hydrophilic coating was disclosed in U.S. Pat. No. 7,217,769 B2, wherein a double bond(alkene) monomer such as N-trimethylsilyl-allylamine (TMSAA), ethylene, propylene and allyl alcohol, was first deposited onto the substrate by plasma grafting and thereby attaching a reactive site for subsequent plasma cross-linking of the hydrophilic molecules bearing a "bifunctional spacer" such as α-hydro-ω-hydroxypoly(oxy-1,2-ethanediyl)-bis-(1-hydroxbenzotriazolyl carbonate) (HPEOC). The method requires the plasma deposition of primary or secondary amine for the subsequent coupling reaction with a "bifunctional" spacer and subsequent bio-conjugation with hydrophilic molecules. The covalent bonding of "prime" coating of primary or secondary amine to the substrate is not guaranteed.

The excitation with high energy irradiation has a low selectivity, bond scissions in the volume of substrate surface and sub-surface are inevitable. The excitation with plasma is very surface specific, however, in addition to the requirement of vacuum, the ablation tendency of the base polymer may be significant. Ulbricht et al., *J AppL Polym. Sci.*, 1995, 56:325. Also, the contribution of the high-energy deep-UV radiation during a direct plasma exposure may lead to an uncontrolled degradation process. Ulbricht, *Polymer,* 2006, 47: 2217-2262. In addition, the delicate topological feature of the surface may be damaged due to the exposure to the irradiation.

Other surface functionalization methods such as oxidative hydrolysis and chemical oxidative etching have also been used to create reactive surface with functional groups such as amino, aldehyde, epoxide, carboxyl, or other reactive groups for subsequent surface modification. These "grafting-to" surface treatments involve harsh condition which may adversely affect the bulk properties and surface morphology.

The above prior arts, regardless of the method being used, requires the steps of surface preparation to create bonding sites, either by chemical treatment to generate radicals on the surface or by physical irradiation activation. Direct coupling on reactive side groups or end groups of the substrate material (e.g. for cellulose derivatives polyamide or polysulfones) has been reported. See Klein, *J. Membr. Sci.,* 2000, 179:1, and Castilho et al., *J. Membr Sci.*, 2000, 172: 269. However, there has been limited success due to the limited availability of reactive functional groups on the surface directly accessible to a surface modifier.

SUMMARY OF THE INVENTION

The present invention overcomes the aforementioned shortcomings by providing a method that can be applied to modify the polymeric surface without the shortcomings of the aforementioned wet chemical or physical irradiation pre-treatment of the surface to afford reactive bonding sites.

A first aspect of the invention is to provide a surface modification method by first forming a surface of primary reactive end groups tethered to the polymer chain ends or side chain ends during fabrication of an article or substrate followed by direct modification with molecules, moieties, organometallic compounds, metal compounds, bio-active molecules, hydrophilic and hydrophobic monomers, oligomers and polymers to attain specific surface properties.

A second aspect of the invention is to provide a method of surface modification using an optional multifunctional coupling agent to couple the primary reactive groups to second reactive groups capable of reacting with the functional groups associated with a surface modifier including bio-active molecule, hydrophilic and hydrophobic monomers, oligomer and polymer to attain specific surface properties. A multifunctional coupling agent is a molecule that can be bound by any mean to two different molecules, such as a functional group on a substrate and a functional group of a bio-active molecule, monomer, oligomer and polymer. A multifunctional coupling agent preferably forms covalent, coordination or ionic bonds with substrate and modifiers to be coupled with.

A third aspect of the invention is to provide a method of creating a surface that has reactive end groups populated on the surface via the surface active spacers linked to the reactive end groups during fabrication of the device.

Another aspect of the invention is to provide a method of creating a surface of reactive end groups with a temporary protecting group. The preferred protecting groups are the ones with surface activity such that upon formation of the surface the protecting groups are populated at the surface and can be selectively removed, leaving the reactive end groups at the surface thereafter and subsequent surface modification.

Yet another aspect of the invention is to provide a method of accelerating the surface enrichment of reactive end groups by subjecting to a conventional thermal process such as extrusion, molding, and annealing.

An additional aspect of the invention is to provide a method of surface modification using a coating composition containing at least one surface active and reactive end group thereby providing a surface with reactive end groups for subsequent bonding of molecules, moieties, organometallic compounds, metal compounds, bio-active molecules, hydrophilic and hydrophobic monomers, oligomers and polymers.

A method of the invention involves bringing reactive end groups to the surface with surface active spacers attached to the polymer chain ends, the surface active spacers promote the migration and enrichment of reactive end groups to the surface during fabrication. A thermal process may be used for fabrication to further encourage the surface enrichment of the reactive end groups. Thermal process may be extrusion, molding, and annealing. The method can be useful for providing medical device a surface with desired properties such as anti-thrombogenic properties, lubricity, selective adsorption, and antimicrobial properties.

Two schematic approaches in accordance with the present invention may be depicted as illustrated in FIGS. 1 and 2. The approach illustrated in FIG. 1 involves direct surface modification with surface active and reactive end groups. The approach illustrated in FIG. 2 illustrates surface modification using a multifunctional coupling agent. In the formulas shown in FIGS. 1 and 2, X represents reactive end groups, Q represents a surface modifying molecule, K represents functional groups associated with molecule Q, Y represents functional groups reactive with X, and Z represents functional groups reactive with K.

In the direct surface modification embodiment illustrated in FIG. 1, the method of this invention comprises the steps of: providing a polymeric body composed of polymeric molecules having first reactive endgroups linked to surface active spacers which surface active spacers comprise endgroups on said polymeric molecules; fabricating an article from said polymeric body and forming a surface of said first reactive endgroups linked to surface active spacers on said polymeric body; and contacting the surface of said polymeric body with a compound containing second reactive endgroups and surface modifying moieties to react said second reactive endgroups with said first reactive endgroups and thereby form covalent, coordination, or ionic bonds linking the surface modifying moieties to the polymeric molecules.

In the multifunctional coupling agent embodiment of the present invention illustrated in FIG. 2, the method comprises the steps of: providing a polymeric body composed of polymeric molecules having first reactive endgroups linked to surface active spacers which surface active spacers comprise endgroups on said polymeric molecules; fabricating an article from said polymeric body and forming a surface of said first reactive endgroups linked to surface active spacers on said polymeric body; contacting the surface of said polymeric body with a compound containing third and fourth reactive endgroups to react said third reactive endgroups with said first reactive endgroups and thereby form covalent or ionic bonds linking the fourth reactive endgroups to the polymeric molecules; and contacting the surface of said polymeric body with a compound containing second reactive groups and surface modifying moieties to react said second reactive endgroups with said fourth reactive endgroups and thereby form covalent, coordination, or ionic bonds linking the surface modifying moieties to the polymeric molecules.

The designations "first reactive endgroups," "second reactive endgroups," "third reactive endgroups," and "fourth reactive endgroups" in this application are employed solely for the purpose of explaining the presently claimed methods in which reactive endgroups fulfill different roles from one another, as is clearly illustrated in FIGS. 1 and 2. The ordinal designations have no significance aside from their use to differentiate different types of reactive endgroup functions in the presently disclosed and claimed methods.

The "first reactive endgroups" mentioned above are normally tethered to surface active spacers as part of polymer chain ends such that the reactive endgroups are spontaneously brought to the surface of an article during the fabrication thereof. The chain ends may be selected from the group consisting of linear polymer chain ends, side chain ends, hyper-branched chain ends, dentrimer chain ends, and chain ends of a polymer network. Fabrication methods usable in the present invention include, without limitation, thermal forming and solvent based processing. The thermal processing may be extrusion, molding, casting, or multilayer processing including co-extrusion and over-molding on top of a base polymer to afford the fabricated article with the surface properties of the polymer containing surface active or reactive endgroups.

During processing in accordance with this invention, the reactive endgroups may be protected by protecting groups such that the functionality and the reactivity of the reactive endgroups are retained during the fabrication of the article. The reactive endgroups may be recovered by a de-protection reaction subsequent to surface formation.

In accordance with this inventive method, the reactive endgroups may be selected from the group consisting of vinyl groups, alkoxy silanes, silanes, epoxy groups, anhydrides, primary amino groups, secondary amino groups, carboxyl groups, aldehyde groups, ketone groups, azide groups, diener, amide groups, isothiocyanate groups, isocyanate groups, halide groups, maleimides, hydroxysuccinimide esters, hydroxysulfosuccinimide esters, imido esters, hydrazines, aziridines, cyano groups, and alkynes. The reactive endgroups are usually selected to be stable toward processing conditions used in fabricating the device or substrate by extrusion, injection molding, or annealing.

The surface active and reactive end groups in the context of the present invention comprise surface active species that exhibit preferential partition at the interface between the polymeric body and its environment in response to an environment which is in direct contact with the surface. The surface active groups may be selected from the group consisting of silicones, substituted or non-substituted alkyl chains, saturated or unsaturated alkyl chains, polyethers, fluorinated alkyl chains, and fluorinated polyethers. The surface modifying moieties may be selected from the group consisting of monomers, oligomers, polymers, organometallic molecules, metal compounds, and bioactive molecules such as chitosan, heparin, hyaluronic acid and its derivatives, antimicrobial agents, antibiotic agents, antithrombogenic agents, peptides, proteins, polypeptides, poly(amino acids), carbohydrates, contrast agents, drugs, glycosaminoglycans, and lubricious substances.

The polymeric substrate in the present method may be selected from the group consisting of solid synthetic polymers, solid natural polymers, and hydrogels. Types of polymers that can be surface-modified in accordance with the novel methods disclosed herein include polyolefins, silicones, acrylic polymers and copolymers, methacrylic polymers and copolymers, fluoropolymers, vinyl polymers and copolymers, polyurethanes, polyurethaneureas, polyester urethanes, silicone polyurethanes, polyvinyl chlorides, polyamides, polyether amides, polyesters, epoxy polymers, polyimides, polyester amides, polyether amides, and silicone hydrogels.

Virtually any type of polymeric article can be surface-modified in accordance with the present invention. In a preferred embodiment, the article is a medical device selected from the group consisting of medical tubing, intravenous bags and catheters, ophthalmic devices, blood filtration devices, cardiovascular devices, biosensors, orthopedic implants, and prostheses.

Finally, the present invention also provides two new types of polymer molecules. One is a polymeric molecule having a surface modifying moiety linked thereto by a molecular linkage comprising the reaction product of a "second" reactive endgroup on a compound containing said second reactive endgroup and said surface modifying moiety with a "first" reactive endgroup which is linked to a surface active spacer that comprises an endgroup on said polymeric molecule—as illustrated in FIG. 1. The other new polymeric molecule has a surface modifying moiety linked to it by a molecular linkage comprising both the reaction product of a second reactive endgroup on a compound containing said second reactive endgroup and said surface modifying moiety with a fourth reactive endgroup on a compound containing third and fourth reactive endgroups and the reaction product of a third reactive endgroup on said compound containing third and fourth reactive endgroups with a first reactive endgroup which is linked to a surface active spacer that comprises an endgroup on said polymeric molecule—as illustrated in FIG. 2.

DETAILED DESCRIPTION OF THE INVENTION

Figure 1:
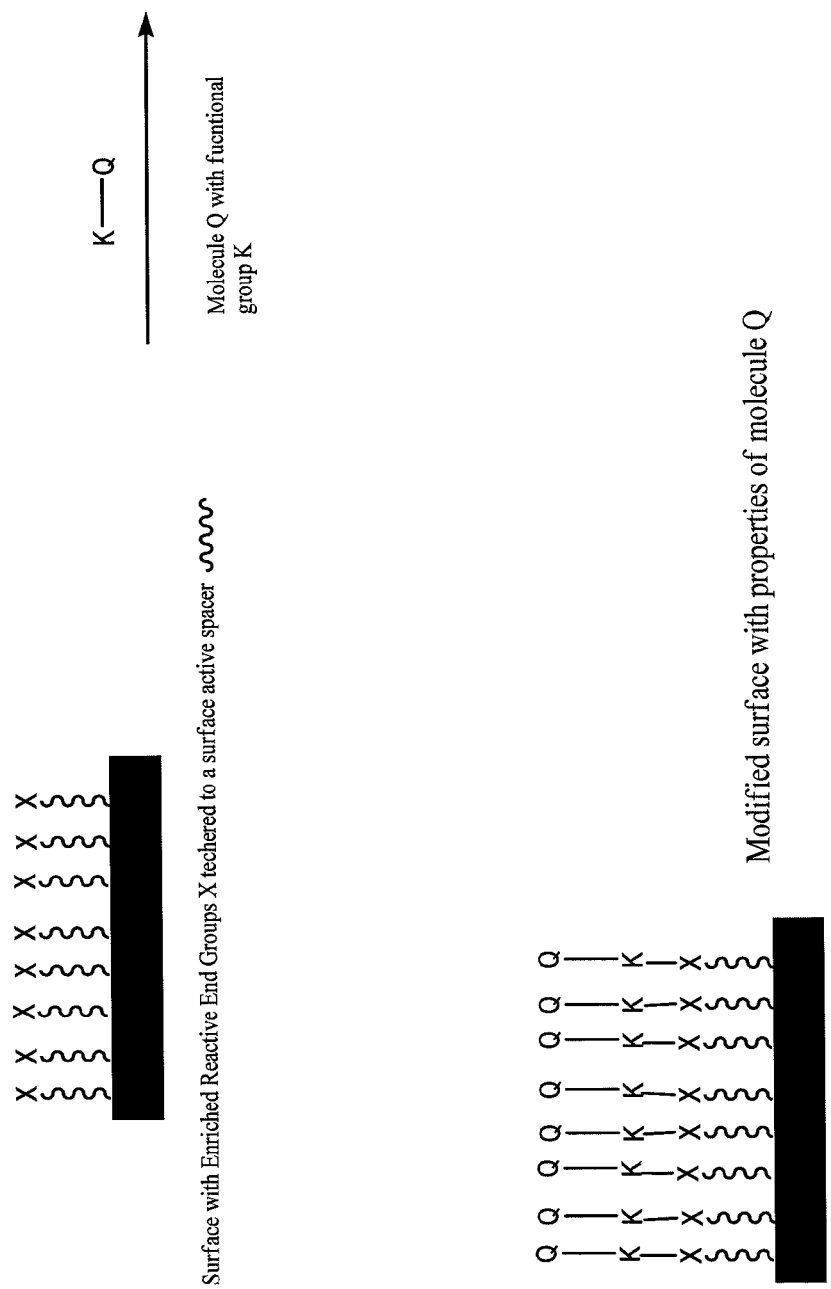
FIG. 1 depicts direct surface modification of a polymer by surface active and reactive end groups in accordance with the present invention.
Figure 2:
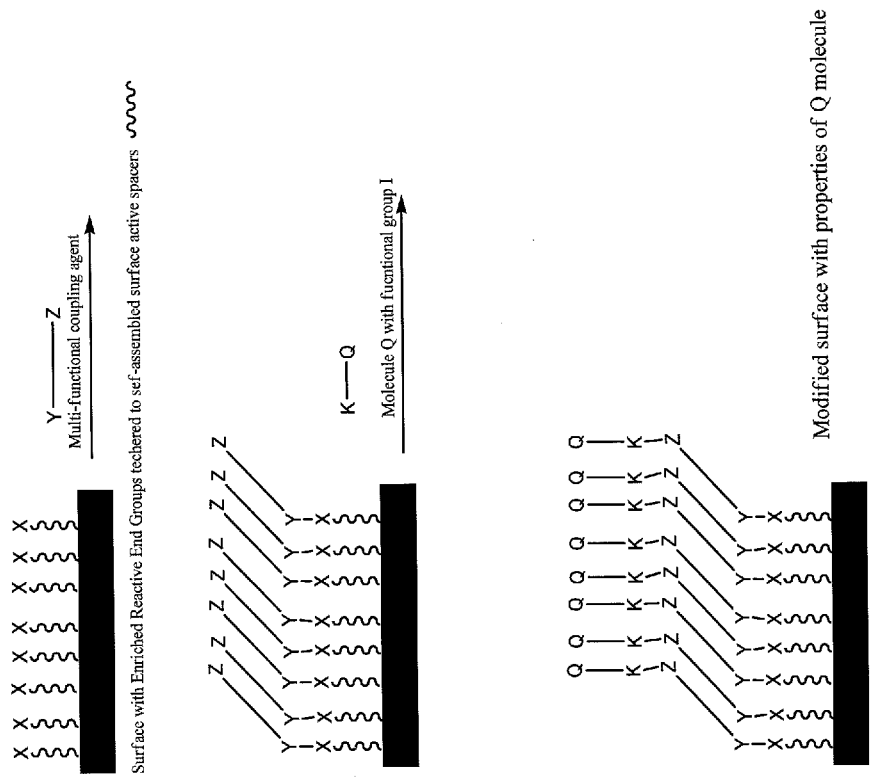
FIG. 2 depicts polymer surface modification using a multifunctional coupling agent in accordance with the present invention.

The present invention is applicable to a variety of polymeric substrates, including but not limited to silicones, polyurethanes, polyamides, polyether amides, polymethacrylates, polyacrylates, polyacrylamides, polyolefins, polysulfones, polyether esters, polyesters, polyimides, polyisobutylenes, and copolymers thereof, which may be used to make medical devices and related bio-affecting materials. With the invention, such devices can be provided with surface modification by reactive end groups at the surface with or without the use of coupling agents, thereby providing the device with altered surface characteristics, such as improved lubriciousness, improved biocompatibility, and specific surface functionality such as selective adsorption of biomolecules for affinity therapy, retention of tear fluid and prevention of protein adsorption for contact lenses, improve permselectivity for biosensor and blood filtration applications, and antimicrobial surfaces.

Thus, according to the invention, biomolecules, monomers, oligomers, polymers and copolymers can be bonded onto polymer substrate to provide a surface with various functions, including but not limited to hydrophilicity, lubricity, biocompatibility, and ability to serve as a primer for subsequent surface modification. The present invention further provides a method for surface modification on inert or difficult-to-adhere-to surfaces, is capable of being applied to both interior and exterior surfaces of the devices, and is relatively convenient and inexpensive.

In accordance with the invention, polymers with surface active and reactive end groups are first synthesized. The reactive end groups are tethered to the surface active spacers as part of the polymer chain ends or side chain ends such that during the manufacturing of medical device, the reactive end groups are spontaneously moved to the surface along with surface active spacers and form a surface constituting of reactive end groups available for further modification. The reactive functional group can be part of the surface active spacer or attached at the end or at the side of the surface active spacer, multiple or singular. The reactive end groups are preferably attached to the surface active spacer at the end.

Various surface active spacers have been used in constructing a self-assembled surface. Examples of chemicals for such application are available from Asemblon™. Those skilled in the art can appreciate that these self-assembling molecules can be further modified to attach a reactive functional group suitable for subsequent surface modification.

Other surface active groups may include, but not limited to silicones, substituted or non-substituted alkyl chains, saturated or un-saturated alkyl chains, polyoxyalkylene-polysiloxanes, polyethers, fluorinated alkyls, fluorinated polyethers, and other surface active species included in WO 2007/142683 A2. Specific examples of such surface active groups include quaternary ammonium molecules as disclosed in U.S. Pat. No. 6,492,445 B2. The quaternary ammonium moieties may have the following formula:

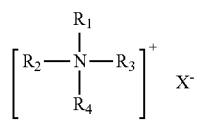

wherein $R_1$, $R_2$, and $R_3$ are radicals of straight or branched or cyclic alkyl groups having one to eighteen carbon atoms or aryl groups and $R_4$ is an amino-, hydroxyl-, isocyanato-, vinyl-, carboxyl-, or other reactive group-terminated alkyl chain capable of covalently bonding to the base polymer. Due to the permanent nature of the immobilized organic biocide, the polymer thus prepared does not release low molecular weight biocide to the environment and has long lasting antimicrobial activity. Alternatively, the surface active endgroup may be an amino group, an isocyanate group, a hydroxyl group, a carboxyl group, a carboxaldehyde group, or an alkoxycarbonyl group, possibly linked to the polymer backbone via a self assembling polyalkylene spacer of different chain lengths, typically between 8 and 24 units. In some specific embodiments, the surface active endgroup may contain a moiety selected from the group consisting of hydroxyl, carboxyl, amino, mercapto, azido, vinyl, bromo, (meth)acrylate, —O(CH$_2$CH$_2$O)$_3$H, —(CH$_2$CH$_2$O)$_4$H, —O(CH$_2$CH$_2$O)$_6$H, —O(CH$_2$CH$_2$O)$_6$CH$_2$COOH, —O(CH$_2$CH$_2$O)$_3$CH$_3$, —(CH$_2$CH$_2$O)$_4$CH$_3$, —O(CH$_2$CH$_2$O)$_6$CH$_3$, trifluoroacetamido, trifluoroacetoxy, and 2',2',2'-trifluorethoxy.

Examples of di-functional fluorinated polyether are available from Solvay Solexis with general structures: X—CF2-O—(CF2-CF2-O)p-(CF2O)q-CF2-X Specific examples are:
FOMBLIN Z DOL 2000, 2500, 4000, X═—CH$_2$OH
FOMBLIN Z DOL TX, X═—CH$_2$(O—CH$_2$—CH$_2$)pOH
FOMBLIN Z TETRAOL, X═—CH$_2$OCH$_2$CH(OH)CH$_2$OH
FOMBLIN AM 2001, AM 3001, X═—CH$_2$O—CH$_2$-pyperonyl Examples of di-functional silicone (HOCH$_2$CH$_2$CH$_2$OCH$_2$CH$_2$CH$_2$)$_2$-[Si(OCH$_3$)$_2$]$_n$ are available from Gelest, Shin-Etsu. Other amine functional silicone fluids such as (H$_2$NCH$_2$CH$_2$CH$_2$OCH$_2$CH$_2$CH$_2$)$_2$—[Si(OCH$_3$)$_2$]$_n$, (H$_2$NCH$_2$CH$_2$CH$_2$)$_2$—[Si(OCH$_3$)$_2$]$_n$, are also available from Wacker and Gelest.

Examples of di-functional alkyl may include 1,12-dodecane diol, 1,14-tetradecane diol, 1,16-hexadecane diol, 1,18-octadecanediol.

Examples of di-carboxylic acid functional alkyl may include 1,14-tetradecanedicarboxylic acid, 1,16-hexadecanedicarboxylic acid, 1,18-octadecanedicarboxylic acid.

Examples of di-amine functional alkyl may include 1,12-dodecane diamine, 1,14-tetradecane diamine, 1,16-hexadecane diamine, 1,18-octadecane diamine.

Depending on the functional groups associated with the surface modifier to be bonded to the surface, polymers with different surface active and reactive end groups can be prepared with the matching reactive end group capable of reacting to a functional group associated with the surface modifier. A surface modifier is a chemical entity that bears certain characteristic desirable for intended application. A reactive group is often associated with the surface modifier to provide the site of chemical bonding.

Reactions of Reactive Endgroups.

It is well known in the art that a pair of matching reactive groups can form a covalent bond or linkage under known coupling reaction conditions, such as, oxidation-reduction, condensation reaction, addition reaction, substitution reaction, cationic or anionic ring opening reaction, Diels-Alder reaction, or Hetero-Diels Alder reaction. For example, a vinyl group reacts with silane group with the presence of catalyst such as Karstedt catalyst, Wilkinson's catalyst, to form a stable Si—C bond; an amino group reacts with aldehyde group to form a Schiff base which may further be reduced to form a stable N—C bond; an amino group reacts with an acid chloride or anhydride to form an amide linkage; an amino group react with isocyanate group to form a urea linkage; an amino group reacts with epoxide to form N—C bond; an hydroxyl reacts with isocyanate to form urethane linkage.

Examples of reactive groups may include without limitation, vinyl group, silane, alkoxy silane, epoxy group, anhydride group, amine group, amide group, hydroxyl group, isocyanate group, isothiocyanate, halide group, acryl chloride, acrylate, methacrylate, aldehyde, carboxylic acid, maleimide, hydroxysuccinimide ester, hydroxysulfosuccinimide ester, imido ester, hydrazine, azide, alkyne, diene, cyano, ketone, thiol, or azeridine.

Preferably, the reactive group is selected from the group consisting of vinyl groups, alkoxy silane, epoxy groups, anhydride, primary amino groups, secondary amino groups, carboxyl groups, aldehyde groups, amide groups, isothiocyanate group, isocyanate groups, halide groups, alkyne groups, diene, ketone, or azeridine. More preferably, the reactive groups selected are stable toward the processing condition used in fabricating the device, even more preferably, the reactive groups are stable under thermal processing condition such as extrusion, injection molding.

Linkages.

Exemplary covalent bonds or linkage formed between pairs of reactive end group and functional group associated with surface modifier may include, without limitation, Si—C bond, Si—O—Si bond, urethane, urea, carbamate, amine, amide, imine, enamine, oxime, amidine, iminoester, carbonate, C—C bond, ether, ester, acetal, sulfonate, sulfide, sulfinate, sulfide, disulfide, sulfinamide, sulfonamide, thioester, thiocarbonate, thiocarbamate, phophonamide, and heterocycles.

Those skilled in the art will appreciate the use of protecting groups to temporary mask the reactive end group such that the reactive end groups are protected while subjecting to the heat, solvent, or in contacting with other components during the fabrication of a device or formation of a surface. The protecting groups can be removed subsequently under mild condition by the known chemistry without imparting physical and morphological properties of the formed surface. More preferably, the protecting groups are the ones with high surface activity, even more preferably with self-assembling ability to maximize the concentration of reactive end groups at the surface. Such protection and de-protection chemistries for many reactive functional groups such as amino group, hydroxyl group, carbonyl group, thiol group, carboxylic group, alkyne group are known to the skilled in the art. For example, a hydroxyl group can be protected by forming ether linkages such as methyl ethers, allyl and benzyl ethers, triphenylmethyl ethers, oxygen-substituted ethers, and silyl ethers. It can also be protected by forming an ester linkage such as acetate ester. The aldehydes and ketones can be protected by forming acetals, thioacetals, enol ethers, enamines A phenol can be protected by using methyl toluene-p-sulfonate to form a methyl ether. The hydroxyl group can be de-protected by known chemistry such as hydrolysis. The carbolic acid groups can be protected by forming esters such as orthoesters. The carboxylic acid can be recovered by the hydrolysis reaction. Amine groups can be protected by forming imines, enamines, amides, carbamates. Thiols can be protected by forming thioethers, acetal derivatives, and thioesters. Other reactive groups such as alkenes, dienes, and alkynes can also be protected by the formation of chemical bonds that can be selectively cleaved under established condition.

Thus, depending on the reactive end groups, various protecting reagents can be used in forming such a temporary bond. One can chose an effective protecting group and de-protecting procedure from well established reference work, such as those described in the text "ACTIVATING AGENTS AND PROTECTING GROUPS, HANDBOOK OF REAGENTS FOR ORGANIC SYNTHESIS," Ed. by Pearson et al, and published by Wiley, June, 1999, ISBN-10: 0471979279, ISBN-13: 978-0471979272. To further facilitate end groups to move to the surface, the protecting groups are preferably surface active. This can be achieved by selecting a protecting reagent that bears surface active moieties or modifying the protecting agents with surface active groups.

For example, trifluoroacetamide (TFA) is commonly used in protecting primary amine in organic synthesis and can be cleaved by a mild hydrolysis in the presence of methyl ester.

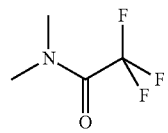

TFA also has high surface activity when exposed to the air and may further assist in concentrating amine end groups at the surface during the formation of a surface.

Silyl ethers are among the most frequently used protective groups for the hydroxyl group, their reactivity and stability can be tailored by varying the nature of the substituents on the silicon. One of the well known silyl ether protective groups used in protecting alcohol is trimethylsilyl ether. For example, one of the hydroxyl groups in aliphatic diol can be selectively protected and the purified product can be used as mono-functional end group in polyurethane synthesis:

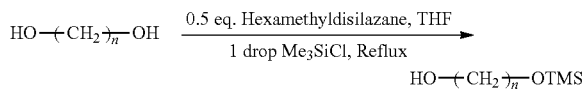

Because the extra mobility and surface activity in minimizing the interfacial free energy, the end groups are kinetically and thermodynamically favored in migrating to and concentrating at the surface, and even form assembled pattern with TMS groups forming the out most layer. Upon treatment with de-protecting agent, the hydroxyl groups can be made available for the subsequent surface modification with functional and bioactive molecules. t-Butyldimethylsilyl ether (TBDMS ether) is another example of popular silyl protective groups used in chemical synthesis and can be introduced under variety condition and readily removed under condition that do not attack other functional groups or chemical bonds.

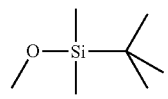

The bulky TBDMS group can be also surface active when exposed to the air and therefore can facilitate the self-concentrating of hydroxyl groups at the surface after cleavage.

It can be understood to the skilled in the art that a multifunctional coupling agent can be used to facilitate the attachment of a surface modifier to a reactive end group at the surface. A multifunctional coupling agent is described as a molecules that bears more than 2 functional groups, each reactive to a reactive end group at the surface and a functional group associated with a surface modifier. The functional groups in the coupling agent can be the same or different. A multifunctional coupling agent that can be bound by any means to two different molecules, such as a reactive group on a substrate surface and a functional group of a surface modifier including bio-active molecules, monomers, oligomers and polymers. A multifunctional coupling agent preferably forms covalent, coordination or ionic bonds with substrate and molecules to be coupled with.

Various multifunctional coupling agents can be found commercially available or can be synthesized. For example, branched polyethylene amine is commercially available from Sigma Aldrich and can be used to couple the aldehyde group at the surface and aldehyde group associated with heparin. Epoxy silane available from Gelest can be used to couple the vinyl group at the surface and amine group associated with amino acids and other biomolecules. Carbodiimide can be used in the coupling of a carboxyl and an amine to form an amide linkage between the molecules being coupled. Examples of carbodiimides includes 1-ethyl-3-(3-dimethylaminopropyl)carbodiimide (EDC), N,N'-dicyclohexylcarbodiimide (DCC), 1-cyclohexyl-3-(2-morpholinoethyl)carbodiimide, diisopropyl carbodiimide, or mixture thereof. Difunctional aldehydes such as glutaraldehyde can be used to immobilize peptide, protein to an amine surface.

It can be understood to those skilled in the art that the method can be applied to a wide variety of medical devices to attain specific surface properties. The properties of interest to the medical usage may include, but not limited to, lubricity, wettability, antimicrobial property, antithrombogenic property, resistance in protein adhesion. For example, heparin bond surfaces are know to have improved thrombo resistance, lubricious surface on urinary Foley catheter is beneficial to reduce the patient discomfort, while lubricious surface on orthopedic implants may reduce the wear and improve the life time of the device. Contact lenses with improved wettability is essential for the maintenance of vision as well as the health of the cornea. It can also be useful for surface modification in diagnostic devices and sensors to improve the separation efficiency.

This invention thus provides medical devices or prostheses which are constituted of polymer bodies, wherein the polymer bodies comprise a plurality of polymer molecules located internally within said body, at least some of which internal polymer molecules have end groups covalently bonded with a surface modifier that comprises a surface of the body. The polymer bodies can include dense, microporous or macroporous components in implantable medical devices or prostheses or in non-implantable disposable or extracorporeal medical devices or diagnostic products. For example, in one embodiment, the polymer body may comprise a membrane component or coating containing immuno-reactants in a diagnostic device. The present invention is particularly adapted to provide such articles configured as implantable medical devices or prostheses or as non-implantable disposable or extracorporeal medical devices or prostheses or as in in vitro or in vivo diagnostic devices, wherein the device or prostheses has a tissue, fluid, and/or blood-contacting surface. Where the article of the present invention is a delivery device, a device for delivering drugs, growth factors, cells, microbes, islets, osteogenic materials, neovascular-inducing moieties, the active agent may be complexed to the surface active and reactive end groups and released through diffusion, or it may be complexed or bonded to surface active and reactive end groups which are chosen to slowly degrade and release the drug over time.

Those skilled in the art will thus appreciate that the present invention provides improved blood gas sensors, compositional sensors, substrates for combinatorial chemistry, customizable active biochips—that is, semiconductor-based devices for use in identifying and determining the function of genes, genetic mutations, and proteins, in applications including DNA synthesis/diagnostics, drug discovery, and immunochemical detection, glucose sensors, pH sensors, blood pressure sensors, vascular catheters, cardiac assist devices, prosthetic heart valves, artificial hearts, vascular stents and stent coatings, e.g., for use in the coronary arteries, the aorta, the vena cava, and the peripheral vascular circulation, prosthetic spinal discs, prosthetic spinal nuclei, spine fixation devices, prosthetic joints, cartilage repair devices, prosthetic tendons, prosthetic ligaments, delivery devices from which the molecules, drugs, cells or tissue are released over time, delivery devices in which the molecules, drugs, cells or tissue are fixed permanently to polymer end groups, catheter balloons, gloves, wound dressings, blood collection devices, blood processing devices, plasma filters, plasma filtration catheters and membranes, devices for bone or tissue fixation or re-growth, urinary stents, urinary catheters, contact lenses, intraocular lenses, ophthalmic drug delivery devices, male and female condoms, devices and collection equipment for treating human infertility, insulation tubing and other components of pacemaker leads and other electrostimulation leads and components such as implantable defibrillator leads, neural stimulation leads, scaffolds for cell, tissue or organ growth/re-growth or tissue engineering, prosthetic or cosmetic breast or pectoral or gluteal or penile implants with or without leak detection capability, incontinence devices, devices for treating acid reflux disease, devices for treating obesity, laparoscopes, vessel or organ occlusion devices, neurovascular stents and occlusion devices and related placement components, bone plugs, hybrid artificial organs containing transplanted tissue, in vitro or in vivo cell culture devices, blood filters, blood tubing, roller pump tubing, cardiotomy reservoirs, oxygenator membranes, dialysis membranes, artificial lungs, artificial livers, or column packing adsorbents or chelation agents for purifying or separating blood, blood cells, plasma, or other fluids. All such articles can be made by conventional means and their surface being modified from surface active and reactive end groups that characterize the polymers described herein.

EXAMPLES

The invention will be further illustrated by the following non-limiting examples:

Example 1

Using surface active and reactive diamine as an end capping agent, a polyurethane with amine terminated end groups can be prepared by a two-step method: I) First, isocyanate terminated polyurethane was prepared in DMAc solution from diisocyanate such as MDI, polyol such as PTMO, PEO, and polyol such as polycarbonate diol, silicone diol, and chain extender such as butane diol, ethylene diamine, ethanol amine, and other short chain diamine, diol, and amino alcohol. The stoichiometric ratio of NCO/H was kept more than 1 so that the polyurethane chain ends were terminated with isocyanate groups, II) Excess amount of surface active and reactive diamine was then added to the reaction mixture to allow the covalent attachment of these end groups at one site, leaving the other amine group for subsequent surface modification. The polymer thus prepared can be used as a coating or can be precipitated and dried for thermal processing such as extrusion, molding. Because of the surface active alkyl chain, the amine groups attached were able to move to the surface of coating, an extruded tubing or injection molded part during processing, enriched or even self-assembled at the surface, making themselves available for subsequent bonding or immobilization of heparin as illustrated in the following formula.

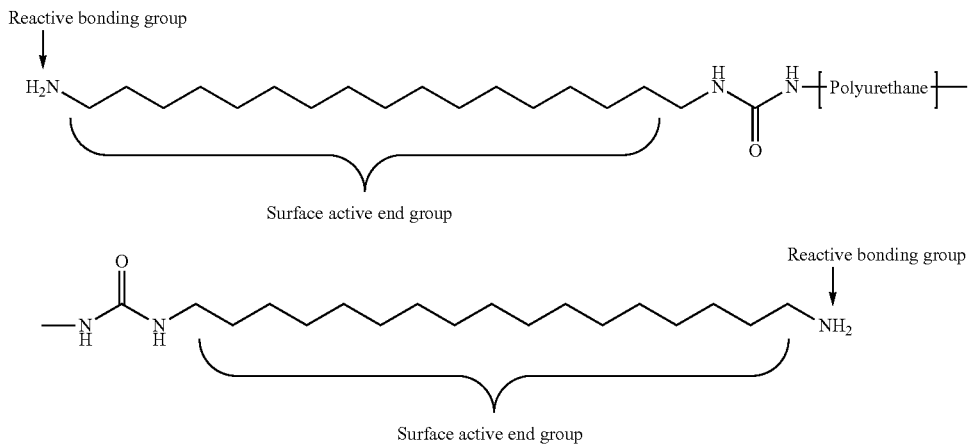

Alternatively, diamine with one end protected with N-t-butoxycarbonyl can be prepared and used in the synthesis of polyurethane. Following the fabrication of an article, these protecting groups concentrated at the surface can be cleaved with selected de-protecting agent under suitable conditions. See FIG. 3.

Figure 3:
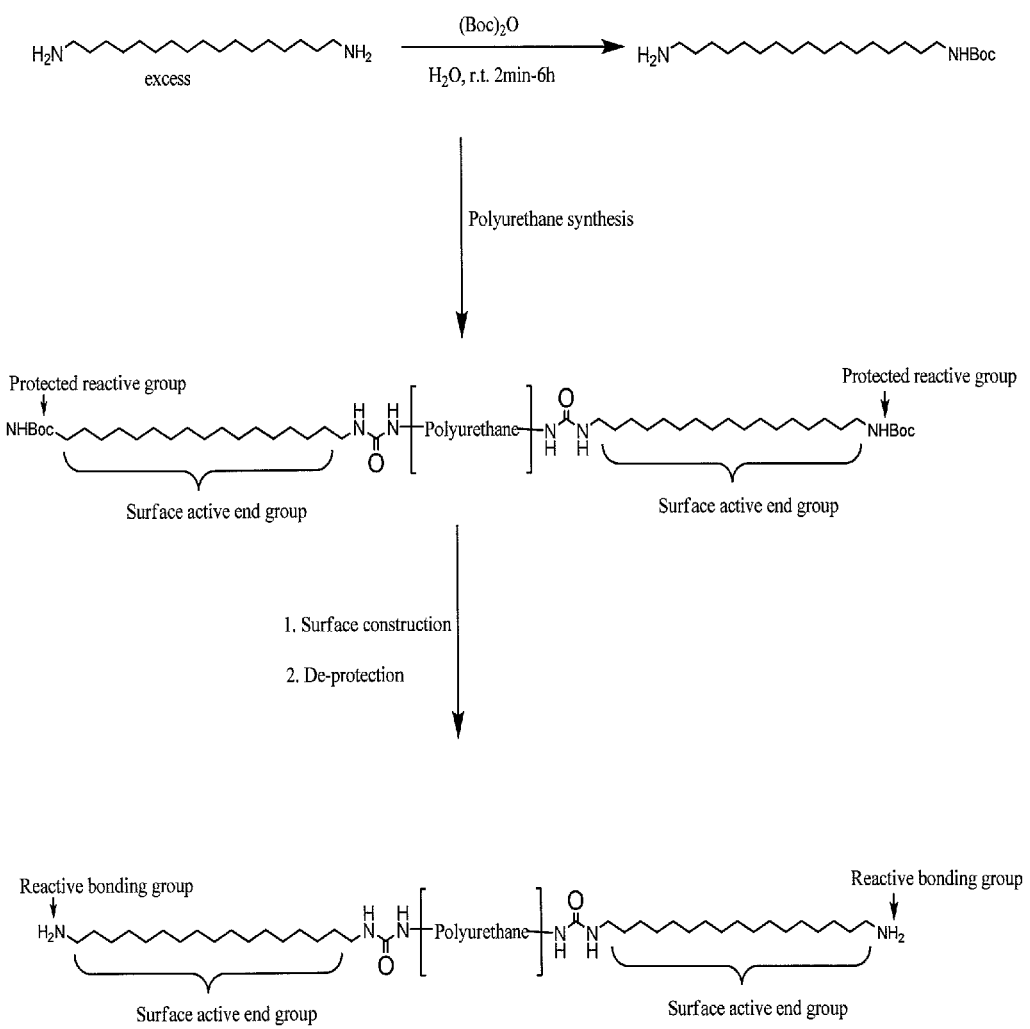
FIG. 3 illustrates cleavage of protecting groups from functional groups following the fabrication of an article in accordance with the present invention.

Polymers thus prepared can be used in fabricating the devices that have protected amine end groups enriched at the surface. Under an environmentally benign condition using mild reagent such as aqueous phosphoric acid, tert-butyl carbamates can be effectively and selectively de-protected, leaving amine groups for subsequent bonding or immobilization of heparin as illustrated in FIG. 3.

Example 2

Figure 4:
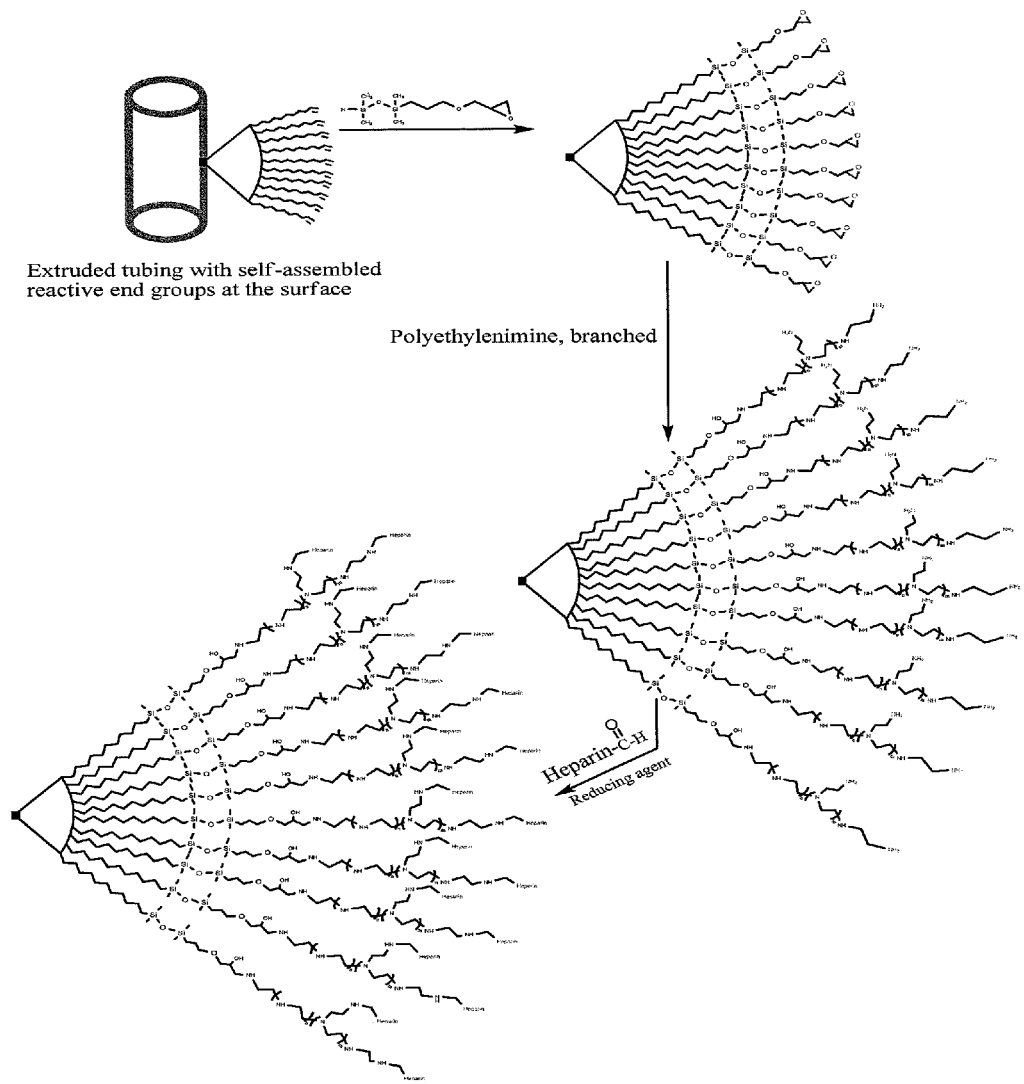
FIG. 4 illustrates epoxy groups reacting with polyamine to form an amine-rich surface which serves as a platform for immobilization of aldehyde-functional heparin in accordance with the present invention.

Polyurethane with 10-undecen-1-ol end groups was first prepared. Tubing was extruded from the resin having the surface enriched with the vinyl end groups which were then reacted with an epoxy silane coupling agent to form a surface abundant with epoxide, the epoxide functional surface can serve as platform for immobilization of hydrophilic molecules such as PVP, PEO, PVA, PMA, polyelectrolytes, and other biomolecules bearing functional group reactive to epoxide to afford wet lubricity. Applying multifunctional hydrophilic molecules may also lock-in the surface with desired properties. Reaction may also take place with underlying reactive end groups due to the penetration/diffusion of surface modifying agents, these underlying end groups will serve as the reservoir for replenishing the surface in demand. Alternatively, the epoxy groups can react with polyamine to form an amine rich surface which can serve as platform for immobilization of biomolecules such as commercially available aldehyde functional heparin, as illustrated in FIG. 4.

Other surface active unsaturated alkyl amine and alcohol includes Oleylamine $CH_3(CH_2)_7CH=CH(CH_2)_8NH_2$, Oleyl alcohol $CH_3(CH_2)_7CH=CH(CH_2)_7CH_2OH$ (CAS#143-28-2), palmitoleyl alcohol $CH_3(CH_2)_5CH=CH(CH_2)_8OH$, elaidyl alcohol $CH_3(CH_2)_7CH=CH(CH_2)_8OH$, erucyl alcohol $CH_3(CH_2)_7CH=CH(CH_2)_{12}OH$, linoleyl alcohol, and hydroxyl terminated unsaturated polybutadiene resins such as the following

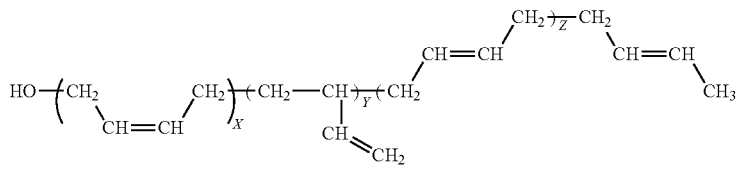

available, for instance, from Sartomer Company, Inc. of Exton, Pa., USA (e.g., as KRASOL resins).

These reactive end groups can be incorporated into polyurethane as surface active end group bearing C=C bonding sites for bio-conjugation or immobilization of specific molecules. Using these hydroxyl-functional surface active and reactive end groups, a thermal plastic polyurethane can be prepared from diisocyanate such as MDI, polyol such as PTMO, PEO, and polycarbonate diol, silicone diol, and chain extender including butane diol, ethylene diamine, ethanol amine, and other short chain diamine, diol, and amino alcohol. Thus an extruded tubing or injection molded part will have the surface active unsaturated alkyl end groups enriched or even self-assembled at the surface and the C=C can be available for subsequent bonding or immobilization, as illustrated below.

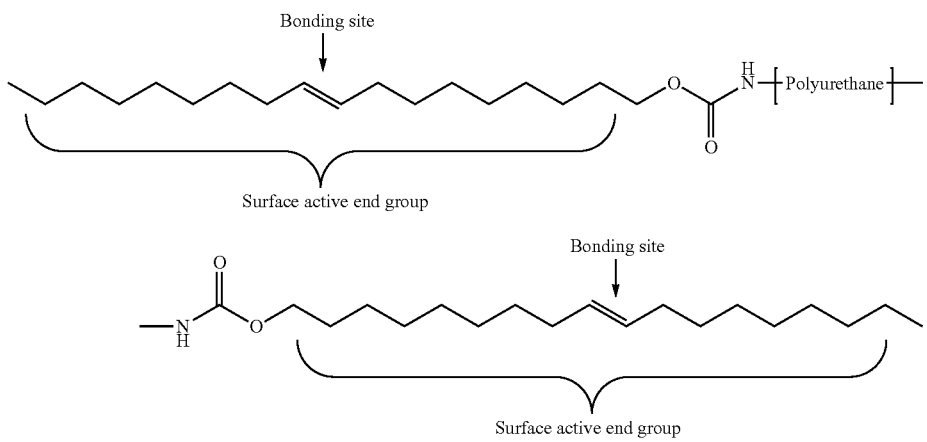

Example 3

Hydroxyl-functional surface active and reactive end groups capping agents can also be optimized and incorporated in polyurethanes as surface active and reactive end group. Examples of such compounds are 11-(9-decenyldimethylsilyl)undecan-1-ol and 11-(triallylsilyl)undecan-1-ol and 11-(triallylsilyl)undecan-1-ol. The synthesis of the molecules is described below:

Synthesis of 11-(9-decenyldimethylsilyl)undecan-1-ol

Figure 5:
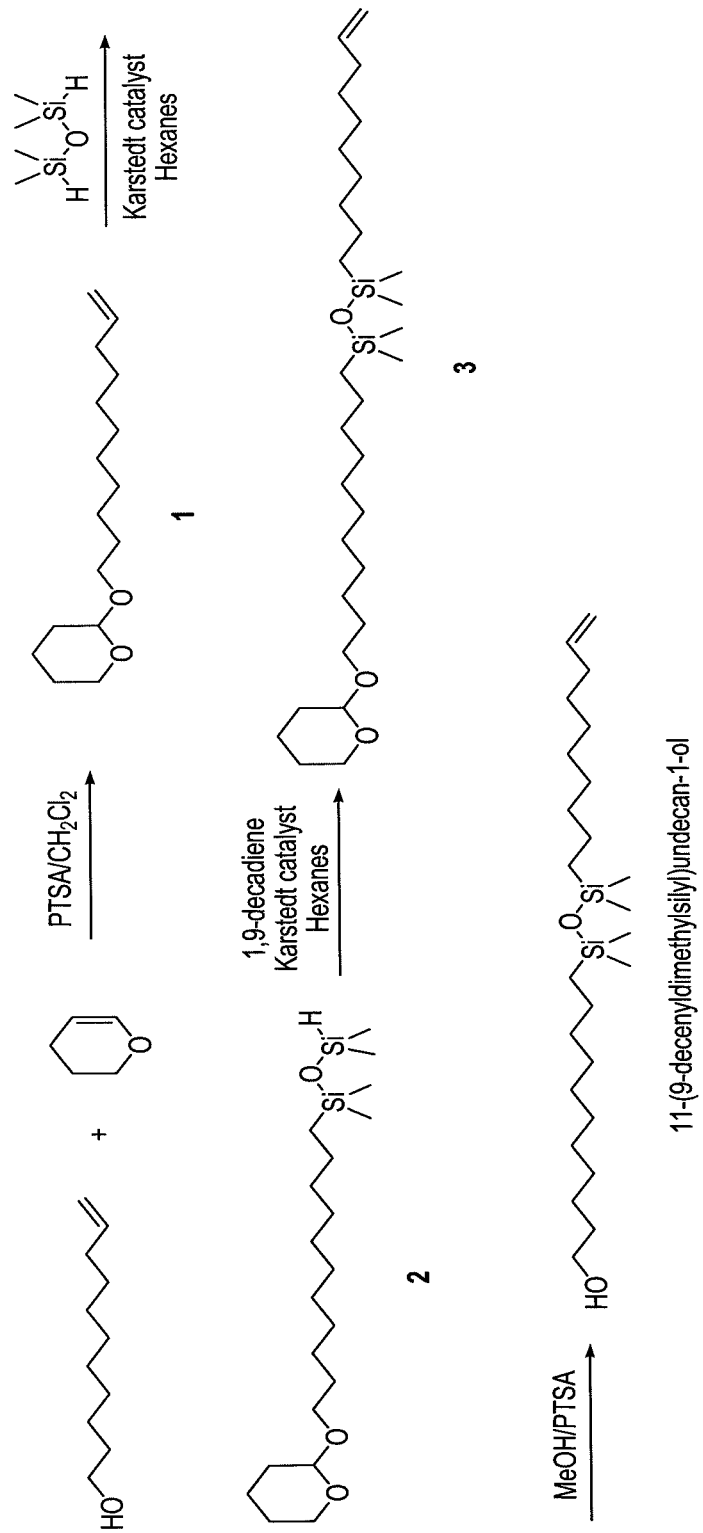
FIG. 5 illustrates the synthesis of 11-(9-decenyldimethylsilyl)undecan-1-ol.

The title compound was synthesized as illustrated in FIG. 5. 10-undecen-1-ol (85 g, 0.5 mol) and p-toluenesulfonic acid monohydrate (0.38 g, 2 mmol) were dissolved in dichloromethane (150 mL) and cooled in ice/water bath under nitrogen. To this solution was then added 3,4-dihydro-2H-pyran (50.4 g, 0.6 mol) dropwise over an hour. After the addition, the solution was stirred for additional two hours in ice/water bath and turned into purple. The solution was then diluted with hexanes (300 mL), washed with aqueous sodium bicarbonate (150 mL×2), and dried over MgSO4. After removal of solvents by rotary evaporation, the residual light brown oil was distilled under vacuum and the distillate at 75-79° C. (300 mTorr) was collected to give THP-protected 10-undecen-1-ol (1) as colorless oil (113 g, 89%). To Compound 1 (6.35 g, 25 mmol) was added Karstedt catalyst (2.1% Pt in xylene, 22 mg) and this mixture was then added into a ice/water bath cooled solution of 1,1,3,3-tetramethydisiloxane (6.7 g, 50 mmol) in hexanes dropwise over 30 min. After the addition, the mixture was stirred for additional three hours in ice/water bath. Solvent and excess 1,1,3,3-tetramethydisiloxane were then removed under vacuum to give the crude intermediate compound 2 as a light brown oil which was then added to a solution of 1,9-decadiene (5.2 g, 37.6 mmol) in hexanes (5 mL) dropwise over 30 min at room temperature. After the addition, the mixture was stirred at room temperature for additional two hours and volatiles were then removed under vacuum to give the residual crude intermediate compound 3 as light brown oil. To this brown oil was then added methanol (50 mL) and p-toluenesulfonic acid monohydrate (0.2 g) and the mixture was stirred at room temperature overnight. After removal of volatiles under reduced pressure, the residual brown oil was purified on silica gel using hexanes/ethyl acetate (85/15, v/v) as eluent to give 2.8 g 11-(9-decenyldimethylsilyl)undecan-1-ol as colorless oil (26.3% over three steps). 1H NMR δ 5.75-5.90 (m, 1H), 4.90-5.05 (m, 2H), 3.60-3.68 (t, 2H), 2.00-2.10 (m, 2H), 1.50-1.62 (m, 2H), 1.20-1.45 (br, 28H), 0.45-0.55 (m, 4H), 0.02 (s, 12H).

Synthesis of 11-(triallylsilyl)undecan-1-ol

Figure 6:
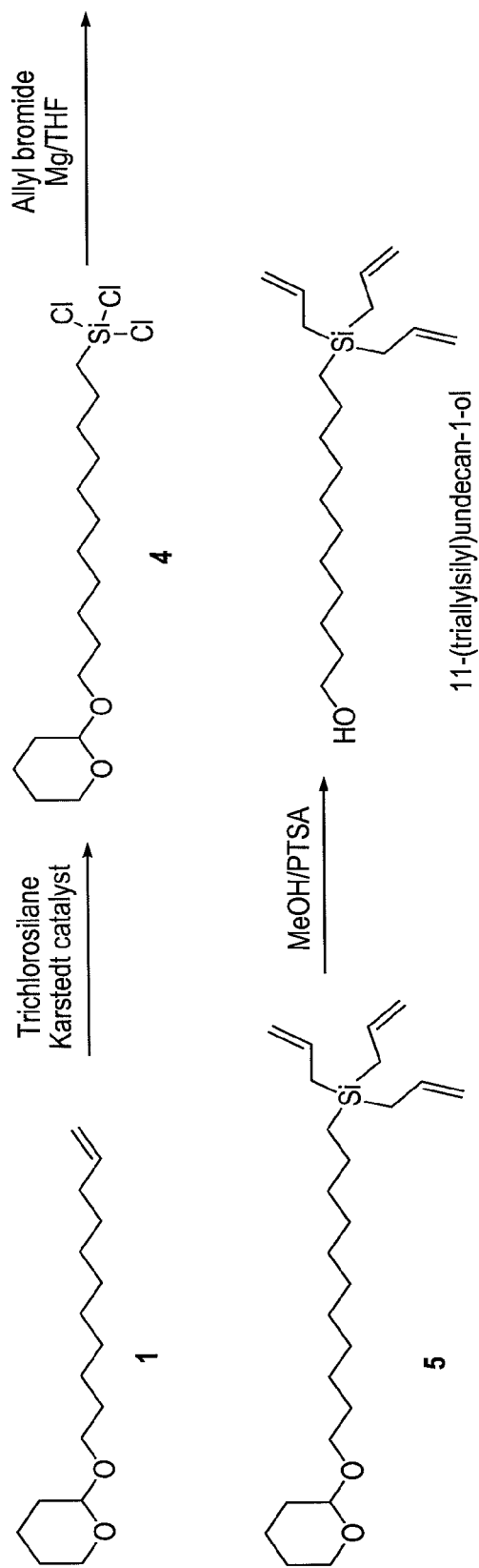
FIG. 6 illustrates the synthesis of 11-(triallylsilyl)undecan-1-ol.

The title compound was synthesized as illustrated in FIG. 6. Compound 1 (7.62 g, 30 mmol), trichlorosilane (32.4 g, 0.24 mol), and Karstedt catalyst (2.1% Pt in xylene, 54 mg) were charged into a 500 mL Schlenk under nitrogen and the mixture was stirred at room temperature for 60 hours. The excess trichlorosilane was then removed under vacuum and the flask was backfilled with nitrogen. Under nitrogen purge, anhydrous THF (200 mL) and granular magnesium (15 g, 0.625 mol) was added to the flask and the flask was then cooled in ice/water bath. Allyl bromide (66 g, 0.54 mol) was then slowly added in over five hours. After the addition, the mixture was stirred at room temperature overnight. Distilled water (250 mL) was then added to quench the reaction. The aqueous layer was extracted with hexanes (100 mL×3) and the combined organic layers was then dried over MgSO4 and concentrated to give a light brown oil which was purified on silica gel using hexanes/ethyl acetate (85/15, v/v) to give 11-(triallylsilyl)undecan-1-ol as a colorless oil (2.2 g, 22.8% over three steps). 1H NMR δ 5.7-5.9 (m, 3H), 4.80-4.95 (m, 6H), 3.60-3.68 (t, 2H), 1.50-1.65 (m, 8H), 1.20-1.40 (br, 16H), 0.50-0.65 (t, 2H).

Another example of a vinyl-substituted functional silicone is:

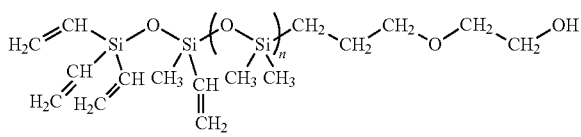

Polyurethane with surface active and reactive vinyl end groups as described above can be synthesized as follows, where the first formula shows monofunctional reactive endgroups and the second formula shows polyfunctional reactive endgroups:

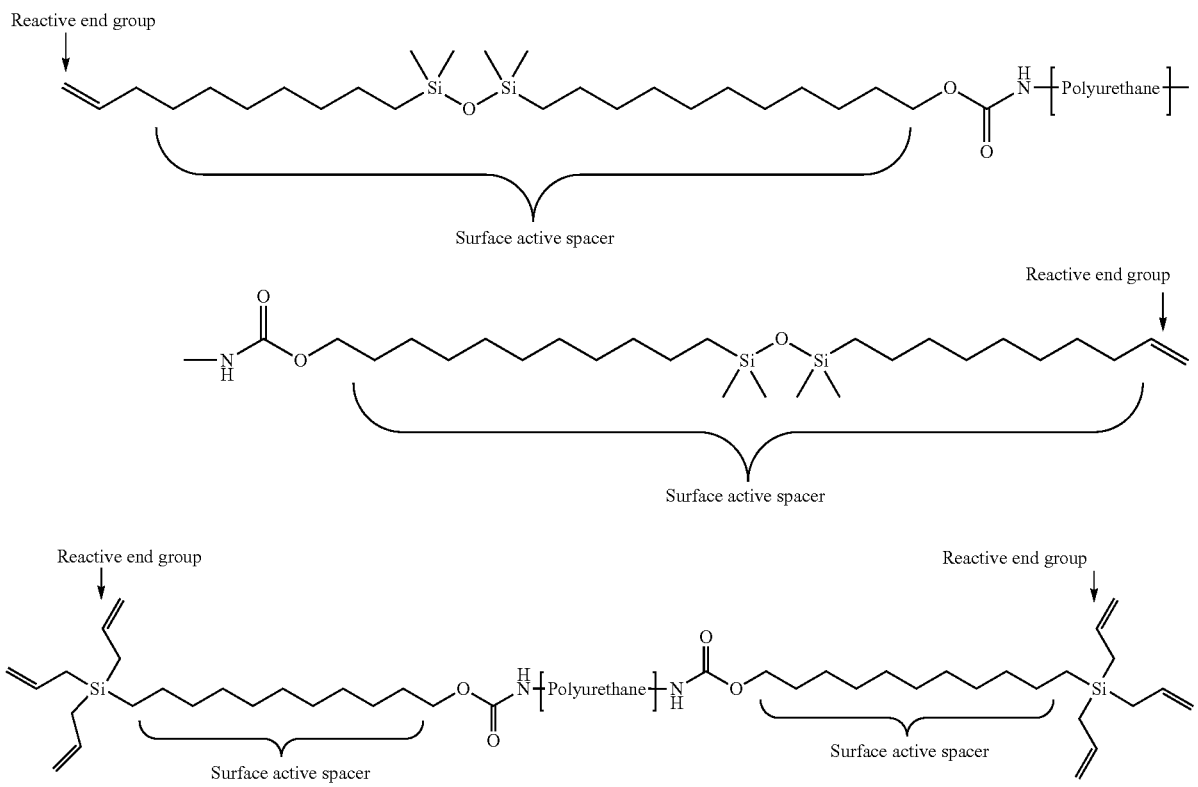

A polyurethane with polyfunctional reactive endgroups as illustrated above was synthesized as follows: To melted MDI was added polycarbonate diol and 11-(triallylsilyl)undecan-1-ol and the reaction was stirred at 70° C. for two hours. The prepolymer was then chain extended with butanediol. Polymer films were prepared by dropping 5 wt % solution of the polymer in THF on glass slides followed by slow evaporation of THF. As comparison, polymer films of polyurethane without surface modifying end group were prepared under the same conditions. A set of films of PU with and without surface modifying end group (11-(triallylsilyl)undecan-1-ol) were immersed into a solution of 0.6 g 2-aminothioethanol and 0.2 g of AIBN in 10 mL of ethanol in a 25 mL round bottom flask. The system was then deoxygenated by bubbling nitrogen through for 30 min. The flask was then kept in a 50° C. oil bath overnight. After being taken out of the flask, the films were flushed with ethanol, dilute HCl, and ethanol sequentially and dried under a nitrogen stream. Static water contact angle of the films of PU with surface modifying end group dropped from 88 degrees for non treated samples to 64 degrees for treated samples as the result of surface modification while the contact angle of the films of PU without SME stayed unchanged at 82 degrees.

The surface of medical device made from polyurethanes with surface active and reactive vinyl end groups can be modified using an epoxy silane, such as that of the formula:

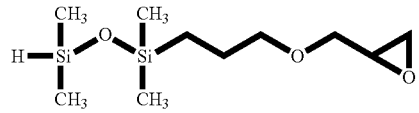

to allow the hydrosilylation reaction between vinyl group tethered to the polymer chain end and silane group of the coupling agent to form C—Si bond thereby attaching epoxide group on the surface for subsequent reaction with polyamine. The excess amine groups can subsequently react with aldehyde group in heparin, leading to the covalent immobilization of the Heparin on the surface.

Example 4

Surface Active and Reactive End Group for Coating and Surface Grafting Application Using a hydroxyl-functional surface active and reactive methacrylate end group having the formula

Figure 7:
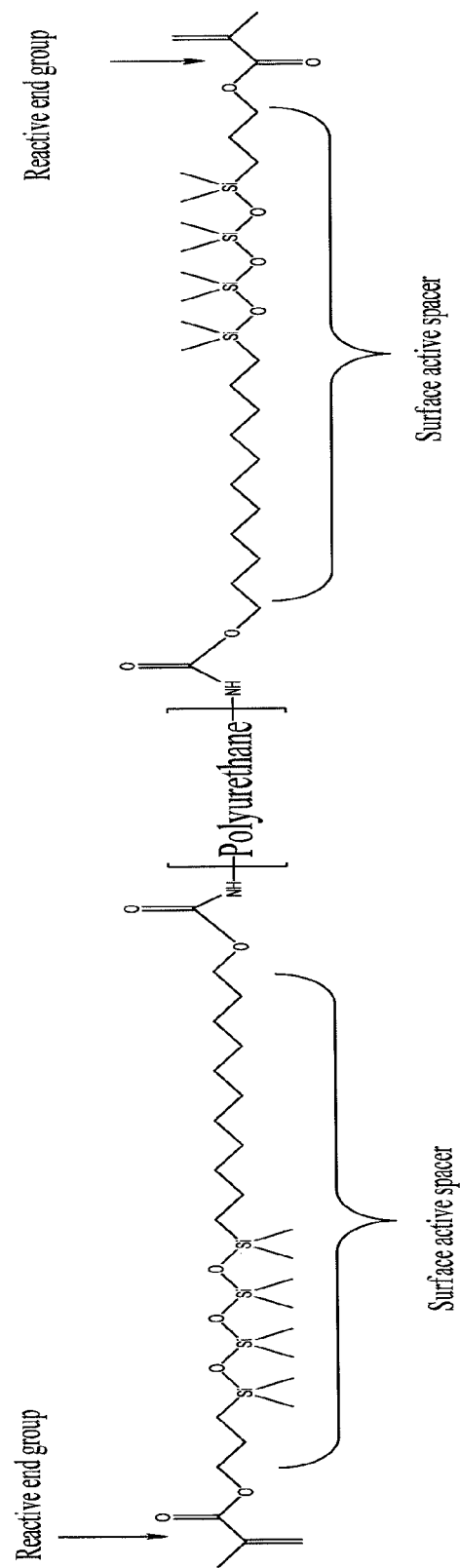
FIG. 7 depicts a polymer in accordance with the present invention having a surface of reactive methacrylate end groups.

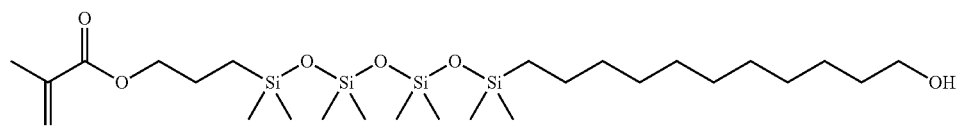 [SMILES: C=C(C)C(=O)OCCC[Si](C)(C)O[Si](C)(C)O[Si](C)(C)O[Si](C)(C)CCCCCCCCCCCO]

a polyurethane coating solution in DMAc can be prepared from diisocyanate such as MDI, polyol such as PTMO, PEO, and polycarbonate diol, silicone diol, and chain extender including butane diol, ethylene diamine, ethanol amine, and other short chain diamine, diol, and amino alcohol. A coating solution thus prepared can provide a surface of reactive methacrylate end groups for further grafting from copolymerization with hydrophilic monomer, macromer and polymers to afford lubricious surface. This surface-modified polymer is depicted in FIG. 7. Examples of hydrophilic monomer includes vinyl pyrrolidone, (meth)acrylamide, PEG (meth) acrylate, PVP (meth)acrylate, (meth)acrylate with charge center, and other (meth)acrylic functional hydrophilic oligomer and polymers. The method can be found especially useful for medical application requiring lubricious surface such as orthopedic device, CVC catheter, urinary catheter, and the like.

Example 5

Polymers with surface active and reactive alkyne end groups or side chains can be synthesized as follows: Using surface active and reactive 15-Hexadecyn-1-ol as an end capping agent, a polyurethane with alkyne terminated end groups can be prepared by a two-step method: I) First, isocyanate terminated polyurethane is prepared in DMAc solution from diisocyanate such as MDI, polyol such as PTMO, PEO, and polyol such as polycarbonate diol, silicone diol, and chain extender such as butane diol, ethylene diamine, ethanol amine, and other short chain diamine, diol, and amino alcohol. II) 0.1-5% of surface active and reactive 15-Hexadecyn-1-ol is added to the reaction mixture to allow the covalent attachment of the hydroxy end groups at one site, leaving the alkyne group for subsequent surface modification.

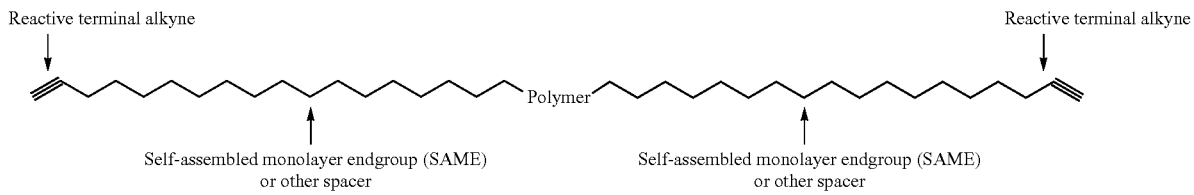

The surface active alkyne can then be reacted by a Huisgen 1,3-dipolar cycloaddition

Figure 8:
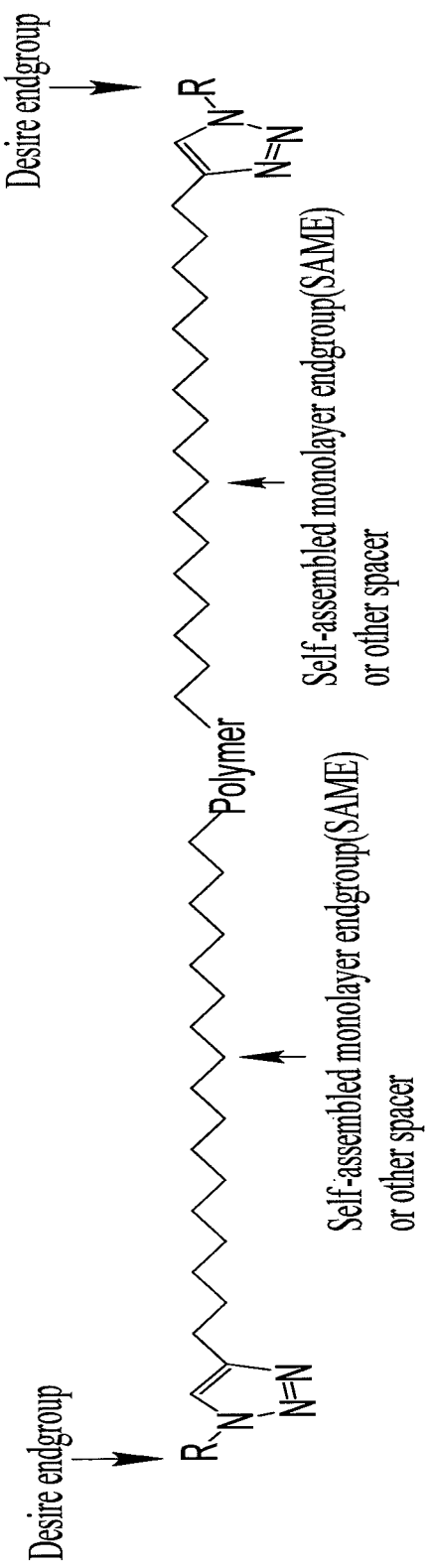
FIG. 8 depicts a post-polymerization surface-modified polymer in accordance with the present invention.

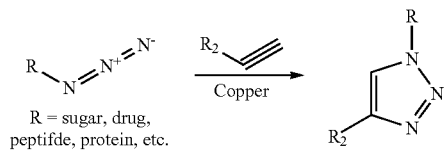

to yield the post-polymerization surface modified polymer depicted in FIG. 8.

End Use Applications

Unconfigured specialized endgroup-containing polymers of this invention may be converted to formed articles by conventional thermoplastic methods used to process polymers, including methods such as extrusion, injection molding, compression molding, calendering, and thermoforming under pressure or vacuum and stereo lithography. Multilayer processing such as co-extrusion or over-molding can be used on top of the base polymers to be economically viable and afford the surface properties from the polymers. The polymers may also be processed by solution-based techniques, such as air brush or airless spraying, ink jet printing, stereo lithography, electrostatic spraying, brushing, dipping, casting, and coating. Water-based polymer emulsions can be fabricated by methods similar to those used for solvent-based methods. In both cases, the evaporation of a volatile liquid (e.g., organic solvent or water) leaves behind a film of the polymer. The present invention also contemplates the use of liquid or solid polymers with specialized endgroups in computer-controlled stereolithography—also know as 3D printing. This method is of particular use in the fabrication of dense or porous structures for use in applications, or as prototypes, for tissue engineering scaffolds, prostheses, medical devices, artificial organs, and other medical, consumer, and industrial end uses. Fabrication considerations which are applicable to the present invention are discussed in U.S. Pat. No. 5,589,563, the contents of which are hereby expressly incorporated by reference.

Polymers used to make useful articles in accordance with this invention will generally have tensile strengths of from about 100 to about 10,000 psi and elongations at break of from about 50 to about 1500%. In some particularly preferred embodiments, porous or non-porous films of the present invention are provided in the form of flexible sheets or in the form of hollow membranes or fibers made by melt blowing, spinning, electrostatic spraying, or dipping, for example. Typically, such flexible sheets are prepared as long rollable sheets of about 10 to 15 inches in width and up to hundreds of feet in length. The thicknesses of these sheets may range from about 5 to about 100 microns. Thicknesses of from about 19 to 25 microns are particularly useful when the article to be manufactured is to be used without support or reinforcement.

Polymer membranes of this invention may have any shape resulting from a process utilizing a liquid which is subsequently converted to a solid during or after fabrication, e.g., solutions, dispersion, 100% solids prepolymer liquids, polymer melts, etc. Converted shapes may also be further modified using methods such as die cutting, heat sealing, solvent or adhesive bonding, or any of a variety of other conventional fabrication methods.

Thermoplastic fabrication methods may also be employed. Membrane polymers made by bulk or solvent-free polymerization method may be cast into a mold during the polymerization reaction. Extrusion, injection molding, calendering, and other conversion methods that are well-known in the art may also be employed to form membranes, films, and coatings of the polymers of the present invention configured into solid fibers, tubing, medical devices, and prostheses. As those skilled in the art will appreciate, these conversion methods may also be used for manufacturing components for non-medical product applications.

This invention thus provides medical devices or prostheses which are constituted of polymer bodies, wherein the polymer bodies comprise a plurality of polymer molecules located internally within said body, at least some of which internal polymer molecules have endgroups that comprise a surface of the body. The polymer bodies can include dense, microporous, or macroporous membrane components in implantable medical devices or prostheses or in non-implantable disposable or extracorporeal medical devices or diagnostic products. For example, in one embodiment, the polymer body may comprises a membrane component or coating containing immuno-reactants in a diagnostic device. The present invention is particularly adapted to provide such articles configured as implantable medical devices or prostheses or as non-implantable disposable or extracorporeal medical devices or prostheses or as in in vitro or in vivo diagnostic devices, wherein the device or prostheses has a tissue, fluid, and/or blood-contacting surface.

Those skilled in the art are also well aware of how to use such embodiments of the present invention. See for instance: Ebert, Stokes, McVenes, Ward, and Anderson, *Biostable Polyurethane Silicone Copolymers for Pacemaker Lead Insulation*, The 28th Annual Meeting of the Society for Biomaterials, Apr. 24-27, 2002, Tampa, Fla.; Ebert, Stokes, McVenes, Ward, and Anderson, *Polyurethane Lead Insulation Improvements using Surface Modifying Endgroups*, The 28th Annual Meeting of the Society for Biomaterials, Apr. 24-27, 2002, Tampa, Fla.; Litwak, Ward, Robinson, Yilgor, and Spatz, *Development of a Small Diameter, Compliant, Vascular Prosthesis*, Proceedings of the UCLA Symposium on Molecular and Cell Biology, Workshop on Tissue Engineering, February, 1988, Lake Tahoe, Calif.; Ward, White, Wolcott, Wang, Kuhn, Taylor, and John, "Development of a Hybrid Artificial Pancreas with Dense Polyurethane Membrane", *ASAIO Journal*, J. B. Lippincott, Vol. 39, No. 3, July-September 1993; Ward, White, Wang, and Wolcott, *A Hybrid Artificial Pancreas with a Dense Polyurethane Membrane: Materials & Design*, Proceedings of the 40th Anniversary Meeting of the American Society for Artificial Internal Organs, Apr. 14-16, 1994, San Francisco, Calif.; Farrar, Litwak, Lawson, Ward, White, Robinson, Rodvien, and Hill, "In-Vivo Evaluation of a New Thromboresistant Polyurethane for Artificial Heart Blood Pumps", *J. of Thoracic Surgery*, 95:191-200, 1987; Jones, Soranno, Collier, Anderson, Ebert, Stokes, and Ward, *Effects of Polyurethanes with SMEs on Fibroblast Adhesion and Proliferation and Monocyte and Macrophage Adhesion*, The 28th Annual Meeting of the Society for Biomaterials, Apr. 24-27, 2002, Tampa, Fla.; and Ward, R. S. and White, K. A., *Barrier Films that Breathe*, CHEMTECH, November, 1991, 21(11), 670, all of which references are hereby expressly incorporated by reference.

INDUSTRIAL APPLICATIONS

The present invention is applicable to a variety of polymeric substrates, including but not limited to silicones, polyurethanes, polyamides, polyether amides, polymethacrylates, polyacrylates, polyacryamides, polyolefins, polysulfones, polyether esters, polyesters, polyimides, polyisobutylenes, and copolymers thereof, which may be used to make medical devices and related bio-affecting materials. With the invention, such devices can be provided with surface modification by reactive end groups at the surface with or without the use of coupling agents, thereby providing the device with altered surface characteristics, such as improved lubriciousness, improved biocompatibility, and specific surface functionality such as selective adsorption of biomolecules for affinity therapy, retention of tear fluid and prevention of protein adsorption for contact lenses, improve permselectivity for biosensor and blood filtration applications, and antimicrobial surfaces.

What is claimed is:

1. A method of modifying a surface on a polymeric substrate selected from the group consisting of solid synthetic polymers, solid natural polymers, and hydrogels, comprising the steps of:

fabricating an article from a polymeric body composed of polymeric molecules having first reactive endgroups tethered to surface active spacers as part of polymer chain ends, which surface active spacers comprise endgroups on said polymeric molecules and forming a surface of said first reactive endgroups linked to surface active spacers on said polymeric body, said polymeric body bearing said first reactive endgroup being an isocyanate-terminated polyurethane;

contacting the surface of said polymeric body with a compound containing at least one third reactive endgroup and at least one fourth reactive endgroup to react said at least one third reactive endgroup with a first reactive endgroup and thereby link said at least one fourth reactive endgroup to the polymeric molecules by a covalent or ionic bond; and contacting the resulting surface of said polymeric body with a compound containing at least one second reactive group and at least one surface modifying moiety, selected from the group consisting of sugars, peptides, and proteins, to react said at least one second reactive endgroup with said at least one fourth reactive endgroup and thereby link said at least one surface modifying moiety to one of said polymeric molecules by a covalent, coordination, or ionic bond, wherein said first and third reactive endgroups and said second and fourth reactive endgroups are respectively selected to be a pair of reactive groups selected from the group consisting of a hydroxyl group and an isocyanate group and a alkyne group and an azido group, and wherein said first reactive endgroups are spontaneously brought to the surface of said article during the fabrication thereof by a fabrication method that comprises thermal forming or solvent-based processing, the polymeric substrate with a modified surface having the formula

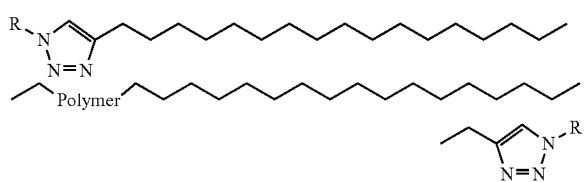

wherein R is a sugar, peptide, or protein moiety and Polymer is a polyurethane.

* * * * *